US00RE39033E

(19) United States
(12) Reissued Patent
Whittemore et al.

(10) Patent Number: US RE39,033 E
(45) Date of Reissued Patent: Mar. 21, 2006

(54) POTENTIATION OF THE MICROBICIDE 2-(THIOCYANOMETHYLTHIO) BENZOTHIAZOLE USING AN N-ALKYL HETEROCYCLIC COMPOUND

(75) Inventors: Marilyn S. Whittemore, Germantown, TN (US); Daniel E. Glover, Brighton, TN (US); S. Rao Rayudu, Germantown, TN (US); Dean T. Didato, Cordova, TN (US)

(73) Assignee: Buckman Laboratories International, Inc., Memphis, TN (US)

(21) Appl. No.: 10/141,079

(22) Filed: May 9, 2002

Related U.S. Patent Documents

Reissue of:
(64) Patent No.: 5,693,631
Issued: Dec. 2, 1997
Appl. No.: 08/456,098
Filed: May 30, 1995

(51) Int. Cl.
*A01N 43/00* (2006.01)
*A01N 43/40* (2006.01)
*A01N 43/64* (2006.01)
*A61K 31/535* (2006.01)

(52) U.S. Cl. ..... 514/183; 8/94.19 R; 8/159; 210/601; 210/612; 210/764; 18/50; 504/100; 514/231.2; 514/315; 514/359; 514/307; 514/408; 514/424

(58) Field of Classification Search ..... 514/183, 514/231.2, 315, 359, 367, 408, 424, 372; 8/94.19 R, 159; 210/601, 612, 764; 18/50; 504/100; 435/29, 7.2, 4; 424/704
See application file for complete search history.

(56) References Cited

U.S. PATENT DOCUMENTS 4,293,559 A * 10/1981 Buckman et al. ..... 514/367
4,479,961 A * 10/1984 Martin ..... 514/367
4,595,691 A * 6/1986 LaMarre et al. ..... 514/367
4,866,081 A * 9/1989 Ito et al. ..... 514/367
4,893,373 A * 1/1990 Kato ..... 15/245
4,944,892 A * 7/1990 Leathers et al. ..... 510/199
4,964,892 A 10/1990 Hsu
5,041,457 A 8/1991 Hsu
5,131,939 A 7/1992 Hsu
5,250,194 A * 10/1993 Hollis et al. ..... 210/764
5,292,763 A 3/1994 Hsu
5,468,759 A 11/1995 Hsu
5,591,760 A 1/1997 Hsu
5,759,786 A 6/1998 Hsu

FOREIGN PATENT DOCUMENTS

DE 24 569 74 6/1976
DE 43 09 690 * 9/1994
JP 06-340504 12/1994
JP 07-69315 3/1995

* cited by examiner

*Primary Examiner*—Herbert J. Lilling
(74) *Attorney, Agent, or Firm*—Nixon Peabody LLP

(57) ABSTRACT

Microbicidal compositions are described. The compositions comprise (a) 2-(Thiocyanomethylthio)benzothiazole (TCMTB) and (b) an N-alkyl heterocyclic compound of the formula:

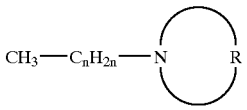

The variable "n" ranges from 5 to 17, and the heterocyclic ring defined by

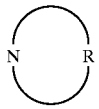

is a substituted or unsubstituted ring having four to eight members. Components (a) and (b) are present in a combined amount effective to control the growth of at least one microorganism. Methods for controlling the growth of microorganisms on various substrates or in aqueous systems are also described. Also described is the industrial application of the microbicidal composition in the leather industry, the lumber industry, the papermaking industry, the textile industry, the agricultural industry, and the coating industry, as well as in aqueous systems.

38 Claims, No Drawings

POTENTIATION OF THE MICROBICIDE 2-(THIOCYANOMETHYLTHIO) BENZOTHIAZOLE USING AN N-ALKYL HETEROCYCLIC COMPOUND

Matter enclosed in heavy brackets [ ] appears in the original patent but forms no part of this reissue specification; matter printed in italics indicates the additions made by reissue.

BACKGROUND OF THE INVENTION

1. Field of the Invention

The present invention relates to compositions for controlling the growth of microorganisms on a variety of substrates and in aqueous systems. More particularly, the invention relates to combinations of 2-(Thiocyanomethylthio) benzothiazole (TCMTB) with an N-alkyl heterocyclic compound and the use of such combinations as microbicides.

2. Background of the Invention

A large variety of commercial, industrial, agricultural, and wood materials or products are subject to microbiologicl attack or degradation which reduces or destroys their economic value. Examples of such materials or products include surface coatings, lumber, seeds, plants, leather and plastics. The various temperatures at which such materials or products are manufactured, stored, or used as well as their intrinsic characteristics make them susceptible to growth, attack, and degradation by common microorgansims such as algae, fungi, yeasts, and bacteria. These microorganisms may be introduced during a manufacturing or other industrial process, by exposure to air, tanks, pipes, equipment, and humans. They can also be introduced while using a material or product, for example, by multiple openings and reclosures of packages or from stirring or removing material with contaminated objects.

Aqueous systems are also highly subject to microbiological growth, attack, and degradation. The aqueous system may be a fresh, brackish or saltwater system. Exemplary aqueous systems include, but are not limited to, latexes, surfactants, dispersants, stabilizers, thickeners, adhesives, starches, waxes, proteins, emulsifying agents, cellulose products, metal working fluids, cooling water, waste water, aqueous emulsions, aqueous detergents, coating compositions, paint compositions, and resins formulated in aqueous solutions, emulsions or suspensions. These systems frequently contain relatively large amounts of water and organic material causing them to be environments well-suited for microbiologic growth and thus attack and degradation.

Microbiological degradation of aqueous systems may manifest itself as a variety of problems, such as loss of viscosity, gas formation, objectionable odors, decreased pH, emulsion breaking, color change, and gelling. Additionally, microbiological deterioration of aqueous systems can cause fouling of the related water-handling system, which may include cooling towers, pumps, heat exchangers, and pipelines, heating systems, scrubbing systems, and other similar systems.

Another objectionable phenomenon occurring in aqueous systems, particularly in aqueous industrial process fluids, is slime formation. Slime formation can occur in fresh, brackish or salt water systems. Slime consists of matted deposits of microorganisms, fibers and debris. It may be stringy, pasty, rubbery, tapioca-like, or hard, and may have a characteristic undesirable odor that is different from that of the aqueous system in which it formed. The microorganisms involved in its formation are primarily different species of spore-forming and nonspore-forming bacteria, particularly capsulated forms of bacteria which secrete gelatinous substances that envelop or encase the cells. Slime microorganisms also include filamentous bacteria, filamentous fungi of the mold type, yeast, and yeast-like organisms. Slime reduces yields in production and causes plugging, bulking, and other problems in industrial water systems.

Various chemicals known as industrial microbicides have been used to prevent microbiological deterioration of industrial systems, raw materials, and products. For instance, 2-(Thiocyanomethylthio)benzothiazole (TCMTB) is a well known, effective microbicide available for such uses. The use of TCMTB as an industrial microbicide has been described in U.S. Pat. Nos. 4,293,559, 4,866,081, 4,595,691, 4,944,892, 4,893,373, and 4,479,961. TCMTB is manufactured by Buckman Laboratories International Inc., and sold as Busan® 30L product, Busan® 30WB product, Busan® 1030 product, Busan® 1118 product as well as other products. TCMTB has the following chemical structure:

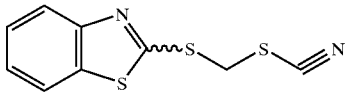

Despite the existence of such microbicides, industry is constantly seeking more cost-effective technology which offers equal or better protection at lower cost and lower concentration. The concentration of conventional microbicides and the corresponding treatment costs for such use, can be relatively high. Important factors in the search for cost-effective microbicides include the duration of microbicidal effect, the ease of use, and the effectiveness of the microbicide per unit weight.

SUMMARY OF THE INVENTION

In view of industry's search for more cost effective microbicides, the present invention offers an improvement over current products or practices.

A first embodiment of the invention provides a microbicidal composition. This compostion comprises (a) 2-(Thiocyanomethylthio)benzothiazole (TCMTB) as a microbicide, and (b) an N-alkyl heterocyclic compound of the formula:

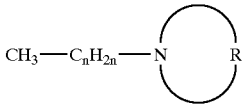

For the N-alkyl heterocyclic compound, n may vary from 5 to 17 and the heterocyclic ring defined by

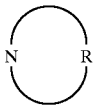

may be a substituted or unsubstituted ring having four to eight members. In the microbicidal composition, the TCMTB (a) and the N-alkyl heterocyclic compound (b) are present in a combined amount effective to control the growth of at least one microorganism. The combination of TCMTB with an N-alkyl heterocyclic compound achieves superior microbicidal activity at lower concentrations and lower cost than TCMTB alone against microbiological attack or degradation such as discussed above.

Another embodiment of the present invention provides a method for controlling the growth of a microorganism on a substrate. This method comprises contacting the substrate with TCMTB and an N-alkyl heterocyclic compound, having the above formula. The TCMTB and N-alkyl heterocyclic compound are present in a combined amount effective to control the growth of at least one microorganism on the substrate.

Another embodiment of the invention provides a method for controlling the growth of microorganisms in an aqueous system capable of supporting growth of a microorganism. This method comprises the step of treating the aqueous system with 2-(Thiocyanomethylthio)benzothiazole (TCMTB) and an N-alkyl heterocyclic compound of the above formula, where the TCMTB and the N-alkyl heterocyclic compound are present in a combined amount effective to control the growth of at least one microorganism in the aqueous system.

The combination of TCMTB and an N-alkyl heterocyclic compound according to the invention is useful in preventing the microbiological attack, degradation, or deterioration of various types of raw materials and products such as leather, textiles, pulp, paper and paperboard, coatings, lumber, as well as agricultural products such as seeds and crops. Advantageously, the combination may be used in various industrial processes used to prepare or manufacture these products. Accordingly, additional embodiments of the present invention employ the combination to control the growth of microorganisms on or in such industrial products, raw materials or processes.

The foregoing and other features and advantages of the present invention will be made more apparent from the following detailed description and preferred embodiments.

DETAILED DESCRIPTION OF THE INVENTION

In one embodiment, the present invention relates to a microbicidal composition comprising 2-(Thiocyanomethylthio)benzothiazole (TCMTB) as a microbicide and an N-alkyl heterocyclic compound. Mixtures of N-alkyl heterocyclic compounds may be used. The TCMTB and the N-alkyl heterocyclic compound are present in a combined amount effective to control the growth of at least one microorganism.

The N-alkyl heterocyclic compounds employed in the present invention have the following general formula:

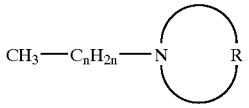

The variable "n" may vary from 5 to 17, and preferably from 9 to 15. Most preferably, n is 11. The alkyl chain defined by $CH_3C_nH_{2n}$— may be branched or unbranched. Branched alkyl chains may lose some of their solubility in water or other aqueous systems. Unbranched alkyl groups are generally preferred.

The heterocyclic ring defined by

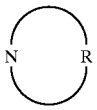

may have four to eight members and is preferably a five-, six-, seven-, or eight-member ring. Most preferably the heterocyclic ring is a six-membered ring.

Although the heterocyclic ring always contains one nitrogen atom, the remainder is generally a carbocycle. However, the ring may contain one or more additional heteroatoms selected from N, O, or S. The ring may be saturated or unsaturated. The ring may also have common substituents such as alkyl groups, substituted alkyl groups, alkenyl groups, substituted alkenyl groups, amino groups, an oxo group to form a cyclic ketone, halogens, etc. The heterocyclic ring may also be part of a multiple ring structure.

The heterocycles listed below exemplify substituted or unsubstituted heterocyclic rings which may be used in the N-alkyl heterocyclic compounds utilized in preferred embodiments of the present invention. Examples of five-membered heterocyclic rings include, but are not limited to, pyrrolidinyl, 2-pyrrolidinonyl, pyrrolinyl, pyrazolidinyl, pyrazolinyl, pyrazolyl, imidazolidinyl, imidazolinyl, imidazolyl and oxazolidinonyl. Six-membered rings include, but are not limited to, piperidinyl, piperazinyl, and morpholinyl. Seven- and eight-membered rings such as hexamethyleneiminyl and heptamethyleneiminyl may also be used in the present invention. One of ordinary skill will appreciate that other heterocyclic rings may also be used.

N-alkyl heterocyclic compounds useful in the invention are available either commercially from chemical supply houses or may be prepared from starting materials using well-known literature methods. U.S. Pat. No. 5,250,194 discloses exemplary methods and is incorporated herein by reference.

U.S. Pat. No. 5,250,194 also describes N-dodecyl heterocyclic compounds and their use as microbicides for aqueous systems to inhibit the growth of microorganisms, the formation of slime in aqueous systems, or the disfigurement or deterioration of substances susceptible to microbiological growth. One example of an N-alkyl heterocyclic compound useful as such a microbicide is N-dodecyl morpholine (DDM). DDM is manufactured by BASF GmbH and by Buckman Laboratories International Inc., Memphis, Tenn.

Preferred N-alkyl heterocyclic compounds for use in the present invention include N-dodecyl morpholine, N-dodecyl imidazole, N-dodecyl-2,6-dimethyl-morpholine, N-dodecyl-5-chloromethyl-2-oxazolidinone, N-dodecyl-2-pyrrolidinone, N-dodecyl hexamethyleneimine, N-dodecyl pyrrolidine, N-dodecyl-3-methyl-piperidine, N-dodecyl piperidine, N-dodecyl-4-methyl-piperidine and N-dodecyl-2-methyl-piperidine. Most preferred of these compounds are N-dodecyl morpholine, (DDM), and N-dodecyl imidazole, (DDI).

Depending on the application, microbicidal compositions according to the present invention may be prepared in various forms known in the art. For example, the composition may be prepared in liquid form as an aqueous solution, dispersion, emulsion, or suspension, a dispersion or suspension in a non-solvent, or as a solution by dissolving the TCMTB and the N-alkyl heterocyclic compound in a solvent or combination of solvents. Suitable solvents include, but are not limited to, methyl ethers of glycols, M-pyrol or petroleum distillates. The microbicidal composition may be prepared as a concentrate for dilution prior to its intended use. Common additives such as surfactants, emulsifiers, dispersants, and the like may be used as known in the art to increase the solubility of the TCMTB or N-alkyl heterocyclic compound in a liquid composition or system, such as an aqueous composition or system. In many cases, the biocidal composition of the invention may be solubilized by simple agitation.

Microbicidal compositions of the present invention may also be prepared in solid form, for example as a powder or tablet, using means known in the art. In a preferred method of preparation, a liquid product containing TCMTB is deposited on a carrier such as diatomaceous earth or kaolin and mixed with an N-alkyl heterocyclic compound in the form of a liquid or solution to form a powder or tablet.

The TCMTB and the N-alkyl heterocyclic compound may be combined in a single composition. Alternatively, the TCMTB and the N-alkyl heterocyclic compound may be employed as separate components such that combined amount for the intended use is effective to control the growth of at least one microorganism.

As mentioned above, a microbicidal composition of the invention demonstrates an unexpected enhanced microbicidal effect between the respective components, TCMTB and an N-alkyl heterocyclic compound. That is, the combination of TCMTB and an N-alkyl heterocyclic compound achieves superior microbicidal activity at lower concentrations to control the growth of microorganisms as compared to the microbicidal capability of TCMTB alone. Thus, the N-alkyl heterocyclic compound potentiates, or even synergistically enhances, the microbicidal effect of the TCMTB. Such a superior effect presents a distinct economic advantage and increases the microbicide's effectiveness per unit weight.

According to the present invention, control of the growth of a microorganism on a substrate or in an aqueous system means control to, at, or below a desired level and for a desired period of time for the particular substrate or system. This can vary from the complete prevention or inhibition of microbiological growth to control at a certain desired level and for a desired time. The combination of TCMTB and N-alkyl heterocyclic compound described here can, in many cases, reduce the total microbiological count to undetectable limits and maintain the count at that level for a significant period of time. Accordingly, the combination may be used to preserve a substrate or system.

The effective amount or percentage of the combination of TCMTB and an N-alkyl heterocyclic compound necessary to achieve the desired result will vary somewhat depending on the substrate or aqueous system to be protected, the conditions for microbial growth, and the degree of protection desired. For a particular application, the amount of choice may be determined by routine testing of various amounts prior to treatment of the entire affected substrate or system. In general, an effective amount used on a substrate ranges from about 0.0001% to about 4% (w/w); preferably about 0.0001% to about 0.2%. With aqueous systems, an effective amount may range from about 0.5 to about 5000 parts per million, more preferably from about 5 to about 1000 parts per million of the aqueous system, and most preferably from, about 10 to about 25 parts per million. Similar amounts effectively control slime formation. For slime control, effective amounts preferably range from about 1 to about 200 parts per million, and more preferably, from about 1 to about 25 parts per million of the aqueous system.

In a preferred embodiment, combinations of TCMTB and an N-alkyl heterocyclic compound are those combinations having a weight ratio of TCMTB to N-alkyl heterocyclic compound from about 99:1 to about 1:99. More preferably the weight ratio is from about 60:10 to about 10:60, and most preferably, from about 50:50 to about 25:75. The weight ratio may vary depending on the intended use, the microorganism encountered as well as the particular material, product, or system to which the combination according to the invention is applied.

The combination of TCMTB and an N-alkyl heterocyclic compound may be applied in a variety of industrial uses and processes for microorganism control. The combination may be used in place of and in the same manner as other microbicides traditionally used in the particular industry. As discussed above, such industries include, but are not limited to the leather industry, the lumber industry, the papermaking industry, the textile industry, the agricultural industry, and the coating industry. The combination of TCMTB and an N-alkyl heterocyclic compound may also be used with aqueous systems such as those previously discussed which are subject to microbiological attack and degradation. The problems caused by microbiological attack and deterioration in these various applications has been described above. The use of the combination of TCMTB and an N-alkyl heterocyclic compound according to the invention to control the growth of microorganisms in particular exemplary applications is described below.

The invention also relates to a method for controlling the growth of microorganisms on various substrates. The method comprises the step of contacting a substrate susceptible to microbiological growth or attack with TCMTB and an N-alkyl heterocyclic compound, as described above. The TCMTB and N-alkyl heterocyclic compound are present in a combined amount effective to control the growth of at least one microorganism on the substrate. Preferably, the method may be used to eliminate or prevent substantially all microbiological growth on the substrate. As discussed above, the TCMTB and the N-alkyl heterocyclic compound may be applied together or as separate compositions. Preferred applications of this general method are discussed below.

In the leather industry, the combination of TCMTB and an N-alkyl heterocyclic compound may be used to control the growth of microorganisms on a hide during a tanning process. To achieve this control, the hide is contacted with a combined amount of TCMTB and an N-alkyl heterocyclic compound effective to control the growth of at least one microorganism on the hide. The combination of the TCMTB and the N-alkyl heterocyclic compound may be used in the tanning process in similar amounts and manner similar to that used to apply other microbicides used in the tanning industry. The type of hide may be any type of hide or skin that is tanned, for example cowhide, snake skin, alligator skin, sheep skin, and the like. The amount used, to some extent, will depend on the degree of microbiological resistance required and may be readily determined by one skilled in the art.

A typical tanning process comprises a number of stages, including, but not limited to, a pickling stage, a chrome-tanning stage, a vegetable-tanning stage, a post-tan washing stage, a retanning stage, a dyeing stage, and a fatliquoring stage. The combination of TCMTB and an N-alkyl heterocyclic compound may be used during all process stages in the tanning process in addition to those stages where a known microbiological problem is occurring. In each stage, the combination of TCMTB and an N-alkyl heterocyclic compound may be a component of the appropriate tanning liquor applied to the hide undergoing tanning.

Incorporating the TCMTB and an N-alkyl heterocyclic compound in a tanning liquor protects the hide from microbiological deterioration during the tanning process. Preferably, the combination is uniformly dispersed, e.g., under agitation, into an appropriate liquor to be used in a tanning process. Typical tanning liquors include, for example, a pickling liquor, a chrome-tanning liquor, a vegetable-tanning liquor, a post-tan washing liquor, a retanning liquor, a dye liquor, and a fatliquor. This method of application ensures that the combination applied to the hides protects against microbiological attack, deterioration, or other microbiological degradation.

In a somewhat analogous nature, the combination of the invention may also be employed to control the growth of microorganisms on a textile substrate in a textile manufacturing process. Contacting the textile substrate with a combination of TCMTB and an N-alkyl heterocyclic compound according to the invention effectively controls the growth of a microorganism on the textile substrate. In a textile process, the combination may be used in similar amounts and a manner similar to other microbicides commonly used in such processes. As one of ordinary skill would appreciate, particular amounts generally depend on the textile substrate and the degree of microbiological resistance required.

The step of contacting the textile substrate with the combination of TCMTB and an N-alkyl heterocyclic compound may be accomplished using means known in the textile art. To control microbiological growth, a textile process generally dips the textile substrate into a bath containing a microbicide, alone or with other chemicals used to treat the textile substrate. Alternatively, the textile substrate may be sprayed with a formulation containing a microbicide. In the bath or the spray, the combination of TCMTB and N-alkyl heterocyclic compound according to the invention are present in a combined amount effective to control the growth of at least one microorganism on the textile substrate. Preferably, the bath and the spray are aqueous-based compositions.

To preserve the value of its raw materials and products, the lumber industry also must control the growth of microorganisms in order to prevent microbiological degradation. The combination of TCMTB and an N-alkyl heterocyclic compound according to the invention is effective to control the growth of microorganisms on lumber.

The combination of TCMTB and an N-alkyl heterocyclic compound may be used to protect the lumber in similar amounts and a similar manner employed for other microbicides used in the lumber industry. Contacting lumber with an effective amount of the combination may be accomplished, for example, by spraying the lumber with an aqueous formulation containing the combination of TCMTB and an N-alkyl heterocyclic compound, by dipping the lumber into a dip bath containing the combination, or other means known in the art. Dipping the lumber in an aqueous bath is preferred.

The TCMTB and the N-alkyl heterocyclic compound are preferably uniformly dispersed in a bath (for example, by agitation) prior to the dipping of the lumber into the bath. In general, the lumber is dipped into the bath, raised, allowed to drip dry, and then air dried. The dip time will depend, as is known in the art, on a variety of factors such as the degree of microbiological resistance desired, the moisture content of the lumber, type and density of the wood, etc. Pressure may be applied to promote penetration of the combination into the lumber being treated. Applying a vacuum to the upper surface of the lumber may also be used to degas the lumber and promote increased wetting of the lumber by a bath containing the microbicidal combination.

The combination of TCMTB and an N-alkyl heterocyclic compound according to the invention also has uses in the agricultural industry. To control the growth of microorganisms on a seed or plant, the seed or plant may be contacted with TCMTB and an N-alkyl heterocyclic compound in a combined amount effective to control the growth of at least one microorganism on the seed or plant. This contacting step may be accomplished using means and amounts known in the agricultural industry for other microbicides. For example, the seed or plant may be sprayed with an aqueous formulation containing the combination of TCMTB and N-alkyl heterocyclic compound, or dipped into a bath containing the combination. After being sprayed or dipped, the seed or plant is generally dried by means known in the art such as drip drying, heated drying, or air drying. For plants or crops, the combination may also be applied using a soil drench. Soil drenching is particularly advantageous when the microorganisms of concern inhabit the soil surrounding the plant.

Yet another aspect of the present invention is a method for controlling the growth of microorganisms in an aqueous system capable of supporting such growth. The aqueous system is treated with TCMTB and an N-alkyl heterocyclic compound such that the TCMTB and N-alkyl heterocyclic compound are present in a combined amount effective to control the growth of at least one microorganism in the aqueous system. This includes controlling, and preferably preventing, slime formation in the aqueous system.

Examples of various aqueous systems include, but are not limited to, latexes, surfactants, dispersants, stabilizers, thickeners, adhesives, starches, waxes, proteins, emulsifying agents, cellulose products, aqueous emulsions, aqueous detergents, coating compositions, paint compositions, alum compositions, and resins formulated in aqueous solutions, emulsions or suspensions. The combination may also be employed in aqueous systems used in industrial processes such as metal working fluids, cooling waters (both intake cooling water and effluent cooling water), and waste waters including waste waters or sanitation waters undergoing treatment of the waste in the water, e.g. sewage treatment.

As with the other uses discussed above, the combination of the invention may be used in the same amounts and in the same manner as microbicides traditionally used in these various aqueous systems. The combination not only protects the aqueous system prior to use or when stored, but in many cases protects the aqueous system when in use or in appropriate applications even after the aqueous system has dried. When used in a paint formulation for example, the combination not only protects the paint in the can, but also the paint film after being applied to a substrate.

Another embodiment of the present invention is a method for controlling the growth of microorganisms on paper or in a papermaking process, e.g., in a pulp or paper slurry and on a finished paper product such as paper board. The paper, pulp, or slurry is contacted with TCMTB and an N-alkyl heterocyclic compound in a combined amount effective to control the growth of at least one microorganism on the paper, the pulp or in a slurry. The contacting step is accomplished using means and amounts known in the papermaking art.

According to this aspect of the invention, for example, a forming web on a papermaking machine (or a wet-lap pulp) may be contacted with the combination of TCMTB and an N-alkyl heterocyclic compound by spraying an aqueous dispersion containing the TCMTB and N-alkyl heterocyclic compound onto the pulp after the pulp leaves the presses in a papermaking process. Or, the TCMTB and the N-alkyl heterocyclic compound may be incorporated into a bath used at the wet or size press and the web contacted by nipping the web to incorporate the combination into the web with any other agents applied at the press. Alternatively, the pulp may be contacted by mixing the TCMTB and N-alkyl heterocyclic compound into the pulp/white water mixture, preferably prior to the pulp reaching the formation wire.

When treating paper (which includes paperboard and other cellulosic products or substrates), the TCMTB and N-alkyl heterocyclic compound may be added into pulp slurries in the headbox, in the substrate forming solution, or in the white water system to treat the water system itself or for incorporation into the body of the paper. Alternatively, as with other known microbicides, the combination of TCMTB and an N-alkyl heterocyclic compound according to the invention may be mixed into a coating used to coat the finished paper.

The activity of the combinations described above has been confirmed using standard laboratory techniques as discussed below. In many cases, the N-alkyl heterocyclic compound potentiates, or even synergistically enhances, the microbicidal affect of the TCMTB.

The following examples are intended to illustrate, not limit, the present invention.

EXAMPLE 1

FUNGICIDAL ACTIVITY OF TCMTB AND AN N-ALKYL HETEROCYCLIC COMPOUND

The fungicidal effects of combinations use of TCMTB and N-alkyl heterocyclic compounds against fungi were measured by the binary dilution method. Combinations of TCMTB and N-dodecyl morpholine (DDM) were tested against a mixture of fungal species isolated from molded chrome-tanned leather. Busan® 30L product, a 30% TCMTB formulation, and BL 2180 product, a 60% formulation of DDM, were used in these tests. Both the Busan® 30L product and BL 2180 product are available from Buckman Laboratories Inc., Memphis, Tenn.

The original Trichoderma culture used in the testing was isolated and cultured from a molded sample of chrome-tanned or wet blue leather. From a suspension of Trichoderma viride spores, 0.1 ml of this suspension was added to each of 200 standard sized test tubes. Each test tube contained 4.5 ml of nutrient salts broth. The test tubes were then agitated to ensure proper mixing of the fungal spores into the nutrient broth. Once inoculated and treated at various concentrations and combinations, the test tubes were incubated at 28° C. for 7 days. The lowest concentration of each chemical compound or combination of compounds that prevented the growth of the fungi in the broth, i.e., the minimum inhibitory concentration, was taken as the endpoint.

Synergism was demonstrated using the method devised by Kull, E. C., Eisman, P. C., Sylwestrwicz, H. D., and Mayer, R. L., Applied Microbiology, 1961, pp.538–541. Kull et al. apply the following summation (synergism index) to determine whether a synergistic effect was achieved:

$$QA/Qa+QB/Qb$$

In this formula QA, Qa, QB, and Qb have the following values:

Qa=Concentration of compound A in parts per million, acting alone, which produced an end point. This represents the minimum inhibitory concentration (MIC) for compound A.

Qb=Concentration of compound B in parts per million, acting alone, which produced an end point. This represents the minimum inhibitory concentration (MIC) for compound B.

QA=Concentration of compound A in parts per million, in the mixture, which produced an end point.

QB=Concentration of compound B in parts per million, in the mixture, which produced an end point.

When the synergism index is greater than one, antagonism is indicated and when the index is equal to one, additivity is indicated. When the index is less than one, synergism exits.

Table 1 below shows the synergism indices as calculated using the Kull method for TCMTB (compound A), dodecyl morpholine (DDM, compound B) and TCMTB/DDM combinations against a mixture of fungal species isolated from molded chrome-tanned leather. The most effective combination tested was found to be 2 ppm Busan® 30L and 6 ppm of BL 2180 product, a 60% DDM formulation.

TABLE 1

| A: Busan ® 30L (30% TCMTB) | B: Dodecyl Morpholine (60% DDM) | Synergism Index |
|---|---|---|
| 4* | 0* | 1 |
| 3 | 2 | 0.75 |
| 2 | 6 | 0.5 |
| 2 | 10 | 0.5 |
| 1.75 | 60 | 0.4375 |
| 0 | 80 | 1 |

*ppm of formulated preparation

EXAMPLE 2

BACTERICIDAL ACTIVITY OF TCMTB AND AN N-ALKYL HETEROCYCLIC COMPOUND

The bactericidal effects of the combined use of TCMTB and N-alkyl heterocyclic compounds against bacteria were measured using an 18 Hour Stokes Broth Test. Combinations of TCMTB and N-dodecyl morpholine (DDM) and of TCMTB and N-dodecyl imidazole (DDI) were tested against the bacteria Sphaerotilus Natans, ATCC 15291. In this test, compound A was Busan® 1030 product, a 30% TCMTB formulation, and compound B was either DDM (99%) or DDI (99%). The Busan® 30L product is available from Buckman Laboratories, Memphis, Tenn.

The Stokes broth substrate used to evaluate effectiveness of microbicidal compositions against Sphaerotilus natans was prepared by adding the following to one liter of water:

| Compound | g/L |
|---|---|
| Peptone | 1.0 |
| Glucose | 1.0 |
| $MgSO_4.7H_2O$ | 0.2 |
| $CaCl_2$ | 0.05 |
| $FeCl_3.6H_2O$ | 0.01 |

The broth was adjusted to pH 7.0 with sodium hydroxide. Forty gram portions were then added to 180 mL Pyrex milk dilution bottles fitted with Escher rubber stoppers and then sterilized. Each of the following substances was then added to each bottle in the order listed.

1. Sterile distilled water as required in each individual case to bring the total weight of the contents of each bottle to 50 g after all subsequent additions specified below (including inoculation with the aqueous suspension of test organism) have been made.
2. Solution of toxicant or control agent to be evaluated in such individual volumes as to give the concentration desired in parts per million by weight.
3. One mL of a 24-hour old S. natans culture grown in Stokes broth.

After the inoculant suspension of the test organism was added to the bottles they were incubated at 28° C. for 18 hours. After this incubation, a 1 mL of sample was withdrawn from each bottle, diluted, plated on Stokes agar, and incubated for 72–96 hr. at 28°–30° C. Stokes agar was prepared like the broth with 12.5 g agar added per liter. The number of colonies on each plate was determined and converted to the count per milliliter of substrate.

From these data, the percentage kills were calculated. The difference between the count for the control substrate (with no toxicant) and the count obtained from the substrate containing toxicant was divided by the count for the control substrate to give the fraction killed, which was then converted to "percentage killed" by multiplying by 100. The results are shown in Tables 2 and 3. A percentage kill of 90 percent or higher represents an extremely useful bactericidal composition. Synergism indices were calculated for some combinations using the Kull method as described in Example 1. Others may be calculated from the data presented.

TABLE 2

| A: Busan ® 1030 (30% TCMTB) | B: Dodecyl Morpholine | CFU/mL | % Kill | Synergism Index |
|---|---|---|---|---|
| 0* | 0 | $3.80 \times 10^6$ | — | |
| 1 | 0 | $1.13 \times 10^6$ | 70.3 | |
| 2 | 0 | $1.09 \times 10^6$ | 71.3 | |
| 5 | 0 | $7.82 \times 10^5$ | 79.4 | |
| 10 | 0 | $<10^3$ | >99.9 | |
| 20 | 0 | $<10^3$ | >99.9 | |
| 0 | 1 | $1.58 \times 10^6$ | 58.4 | |
| 0 | 2 | $1.24 \times 10^6$ | 67.4 | |
| 0 | 5 | $8.51 \times 10^5$ | 77.6 | |
| 0 | 10 | $<10^3$ | >99.9 | |
| 0 | 20 | $<10^3$ | >99.9 | |
| 1 | 1 | $1.02 \times 10^6$ | 73.2 | |
| 1 | 2 | $6.33 \times 10^5$ | 83.3 | |
| 1 | 5 | $2.17 \times 10^4$ | 99.4 | 0.60 |
| 1 | 10 | $<10^3$ | >99.9 | |
| 2 | 1 | $1.14 \times 10^3$ | 97.0 | 0.30 |
| 2 | 2 | $1.85 \times 10^5$ | 95.1 | 0.40 |
| 2 | 5 | $6.41 \times 10^3$ | 83.1 | |
| 2 | 10 | $<10^3$ | >99.9 | |
| 5 | 1 | $1.23 \times 10^3$ | 96.8 | 0.60 |
| 5 | 2 | $8.74 \times 10^4$ | 97.7 | 0.70 |
| 5 | 5 | $<10^3$ | >99.9 | 1.00 |
| 5 | 10 | $<10^3$ | >99.9 | |
| 10 | 1 | $<10^3$ | >99.9 | |
| 10 | 2 | $<10^3$ | >99.9 | |
| 10 | 5 | $<10^3$ | >99.9 | |
| 10 | 10 | $<10^3$ | >99.9 | |

*ppm of formulated preparation

TABLE 3

| A: Busan ® 1030 (30% TCMTB) | B: Dodecyl Morpholine | CFU/mL | % Kill | Synergism Index |
|---|---|---|---|---|
| 0* | 0 | $5.05 \times 10^6$ | — | |
| 0.2 | 0 | $2.63 \times 10^6$ | 47.9 | |
| 0.5 | 0 | $1.97 \times 10^6$ | 61.0 | |
| 1 | 0 | $1.17 \times 10^6$ | 76.8 | |
| 2 | 0 | $1.06 \times 10^6$ | 79.0 | |
| 5 | 0 | $8.20 \times 10^3$ | 83.8 | |
| 10 | 0 | $<10^3$ | >99.9 | |
| 20 | 0 | $<10^3$ | >99.9 | |
| 0 | 1 | $1.26 \times 10^6$ | 75.1 | |
| 0 | 2 | $6.80 \times 10^3$ | 86.5 | |
| 0 | 5 | $<10^3$ | >99.9 | |
| 0 | 10 | $<10^3$ | >99.9 | |

TABLE 3-continued

| A: Busan ® 1030 (30% TCMTB) | B: Dodecyl Morpholine | CFU/mL | % Kill | Synergism Index |
|---|---|---|---|---|
| 0 | 20 | $<10^3$ | >99.9 | |
| 0 | 50 | $<10^3$ | >99.9 | |
| 0 | 100 | $<10^3$ | >99.9 | |
| 0.2 | 2 | $1.04 \times 10^6$ | 79.4 | |
| 0.2 | 5 | $<10^3$ | >99.9 | 1.02 |
| 0.2 | 10 | $<10^3$ | >99.9 | |
| 0.2 | 20 | $<10^3$ | >99.9 | |
| 0.5 | 1 | $8.40 \times 10^3$ | 83.4 | |
| 0.5 | 2 | $5.00 \times 10^5$ | 90.1 | 0.45 |
| 0.5 | 5 | $<10^3$ | >99.9 | |
| 0.5 | 10 | $<10^3$ | >99.9 | |
| 0.5 | 20 | $<10^3$ | >99.9 | |
| 1 | 1 | $3.80 \times 10^3$ | 92.5 | 0.30 |
| 1 | 2 | $7.70 \times 10^5$ | 84.8 | |
| 1 | 5 | $1.25 \times 10^6$ | 75.2 | |
| 1 | 10 | $<10^3$ | >99.9 | |
| 1 | 20 | $<10^3$ | >99.9 | |
| 2 | 1 | $3.50 \times 10^5$ | 93.1 | 0.40 |
| 2 | 2 | $6.50 \times 10^5$ | 87.1 | |
| 2 | 5 | $<10^3$ | >99.9 | |
| 2 | 10 | $<10^3$ | >99.9 | |

*ppm of formulated preparation

EXAMPLE 3

BACTERICIDAL ACTIVITY OF TCMTB AND AN N-ALKYL HETEROCYCLIC COMPOUND

The bactericidal effects of the combined use of TCMTB and N-alkyl heterocyclic compounds against bacteria were measured using an 28 Day API Test. Combinations of TCMTB (compound A) and N-dodecyl morpholine (DDM, compound B) and of TCMTB (compound A) and N-dodecyl imidazole (DDI, compound B) were tested against the bateria Desulfovibrio desulfuricans, ATCC 7757. Busan® 1030 product, a 30% TCMTB formulation, DDM (99%), and DDI (99%) were used in this testing. The Busan® 30L product is available from Buckman Laboratories, Memphis, Tenn.

The medium used was a modified API Broth having the following composition:

| Compound | g/L |
|---|---|
| Yeast extract | 5.0 |
| Ascorbic acid | 0.1 |
| Sodium lactate | 5.2 |
| $MgSO_4.7H_2O$ | 0.2 |
| $K_2HPO_4$ | 0.6 |
| Ferrous ammonium sulfate | 0.1 |
| NaCl | 10.0 |

The compounds were dissolved in 1.0 L of deionized water to form the medium. The pH of the medium was adjusted to a final pH of 6.9 with 1N sodium hydroxide prior to sterilization.

The medium was sterilized at 121° C. for 20 minutes and then allowed to cool to room temperature. The medium is then inoculated by adding 10 ml per liter of a 24-hr. broth culture of Desulfovibrio desulfuricans.

From stock solutions of the chemicals to be tested, sufficient amounts of the compounds were added to 1 oz. glass bottles so that when a bottle was completely filled, the desired concentration of the chemical was present. The bottles were then completely filled with the inoculated API broth (10 mL innoculum per liter medium) in a manner such as to exclude all air and provide an anaerobic state. The bottles were capped tightly and inverted gently to mix the contents and, at the same time, to make sure no air bubbles were present.

Incubation was carried out at 37° C. for 28 days. Growth was indicated by blackening of the culture medium, whereas those bottles having sufficient chemical to inhibit growth would remain clear. Observations of growth were made at the end of 7 days, 14 days, 21 days and 28 days. Results were reported using a scale of 0 to 4, where 0=no growth and 4=heavy growth.

The results are shown in Tables 4 and 5. The minimum inhibitory concentration (MIC) was defined as the lowest concentration tested which gave no growth in the bottle (clear liquid). Synergism indices were calculated for some combinations using the Kull method as described in Example 1. Others may be calculated from the data presented.

TABLE 4

| A: Busan ® 1030 (30% TCMTB) | B: Dodecyl Morpholine | Day 7 | Day 14 | Day 21 | Day 28 | Synergism Index |
|---|---|---|---|---|---|---|
| 0* | 0 | 4 | 4 | 4 | 4 | |
| 10 | 0 | 4 | 4 | 4 | 4 | |
| 20 | 0 | 0 | 2 | 3 | 4 | |
| 40 | 0 | 0 | 0 | 0 | 0 | |
| 80 | 0 | 0 | 0 | 0 | 0 | |
| 160 | 0 | 0 | 0 | 0 | 0 | |
| 0 | 10 | 4 | 4 | 4 | 4 | |
| 0 | 20 | 4 | 4 | 4 | 4 | |
| 0 | 40 | 2 | 3 | 4 | 4 | |
| 0 | 80 | 0 | 1 | 3 | 4 | |
| 0 | 160 | 0 | 0 | 2 | 3 | |
| 0 | 320 | 0 | 0 | 0 | 0 | |
| 5 | 10 | 4 | 4 | 4 | 4 | |
| 5 | 20 | 4 | 4 | 4 | 4 | |
| 5 | 40 | 4 | 4 | 4 | 4 | |
| 5 | 80 | 0 | 2 | 4 | 4 | |
| 5 | 160 | 0 | 0 | 0 | 0 | 0.63 |
| 10 | 10 | 4 | 4 | 4 | 4 | |
| 10 | 20 | 2 | 3 | 4 | 4 | |
| 10 | 40 | 1 | 2 | 3 | 4 | |
| 10 | 80 | 0 | 0 | 0 | 0 | 0.50 |
| 10 | 160 | 0 | 0 | 0 | 0 | |
| 20 | 10 | 4 | 4 | 4 | 4 | |
| 20 | 20 | 0 | 0 | 0 | 0 | 0.56 |
| 20 | 40 | 0 | 0 | 0 | 0 | |
| 20 | 80 | 0 | 0 | 0 | 0 | |
| 20 | 160 | 0 | 0 | 0 | 0 | |
| 40 | 10 | 0 | 0 | 0 | 0 | |
| 40 | 20 | 0 | 0 | 0 | 0 | |
| 40 | 40 | 0 | 0 | 0 | 0 | |
| 40 | 80 | 0 | 0 | 0 | 0 | |
| 40 | 160 | 0 | 0 | 0 | 0 | |

*ppm of formulated preparation

TABLE 5

| A: Busan ® 1030 (30% TCMTB) | B: Dodecyl Morpholine | Day 7 | Day 14 | Day 21 | Day 28 | Synergism Index |
|---|---|---|---|---|---|---|
| 0* | 0 | 4 | 4 | 4 | 4 | |
| 10 | 0 | 4 | 4 | 4 | 4 | |
| 20 | 0 | 0 | 2 | 3 | 4 | |
| 40 | 0 | 0 | 0 | 0 | 0 | |
| 80 | 0 | 0 | 0 | 0 | 0 | |
| 160 | 0 | 0 | 0 | 0 | 0 | |
| 0 | 1 | 4 | 4 | 4 | 4 | |

TABLE 5-continued

| A: Busan ® 1030 (30% TCMTB) | B: Dodecyl Morpholine | Day 7 | Day 14 | Day 21 | Day 28 | Synergism Index |
|---|---|---|---|---|---|---|
| 0 | 2 | 4 | 4 | 4 | 4 | |
| 0 | 4 | 4 | 4 | 4 | 4 | |
| 0 | 8 | 2 | 4 | 4 | 4 | |
| 0 | 16 | 0 | 0 | 0 | 0 | |
| 0 | 32 | 0 | 0 | 0 | 0 | |
| 5 | 2 | 4 | 4 | 4 | 4 | |
| 5 | 4 | 4 | 4 | 4 | 4 | |
| 5 | 8 | 0 | 0 | 0 | 0 | 0.63 |
| 5 | 16 | 0 | 0 | 0 | 0 | |
| 10 | 1 | 4 | 4 | 4 | 4 | |
| 10 | 2 | 4 | 4 | 4 | 4 | |
| 10 | 4 | 0 | 2 | 3 | 4 | |
| 10 | 8 | 0 | 0 | 0 | 0 | 0.75 |
| 10 | 16 | 0 | 0 | 0 | 0 | |
| 10 | 32 | 0 | 0 | 0 | 0 | |
| 20 | 1 | 4 | 4 | 4 | 4 | |
| 20 | 2 | 0 | 2 | 3 | 4 | |
| 20 | 4 | 0 | 0 | 0 | 0 | 0.75 |
| 20 | 8 | 0 | 0 | 0 | 0 | |
| 20 | 16 | 0 | 0 | 0 | 0 | |
| 40 | 1 | 0 | 0 | 2 | 4 | |
| 40 | 2 | 0 | 0 | 0 | 0 | |
| 40 | 4 | 0 | 0 | 0 | 0 | |
| 40 | 8 | 0 | 0 | 0 | 0 | |
| 40 | 16 | 0 | 0 | 0 | 0 | |

*ppm of formulated preparation

The invention claimed is:

1. A microbicidal composition comprising:

(a) 2-(Thiocyanomethylthio)benzothiazole (TCMTB) and (b) an N-alkyl heterocyclic compound of the formula:

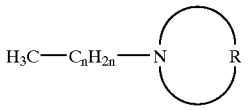

wherein n varies from [5 to 17] *9 to 15*, the heterocyclic ring defined by

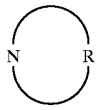

is a substituted or unsubstituted ring having four to eight members, and wherein the TCMTB (a) and the N-alkyl heterocyclic compound (b) are present in a combined amount effective to control the growth of at least one microorganism and the [and the] amount of the N-alkyl heterocyclic compound (b) present potentiates the microbicidal activity of the TCMTB (a).

2. A microbicidal composition according to claim 1, wherein [n varies from 9 to 15, and] the heterocyclic ring is selected from the group consisting of pyrrolidinyl, 2-pyrrolidinonyl, pyrrolinyl, pyrazolidinyl, pyrazolinyl, pyrazolyl, imidazolidinyl, imidazolinyl, imidazolyl, oxazolidinonyl, piperidinyl, piperazinyl, morpholinyl, hexamethyleneiminyl, and heptamethyleneiminyl.

3. A microbicidal composition according to claim 1, wherein the N-alkyl heterocyclic compound is selected from the group consisting of N-dodecyl morpholine, N-dodecyl imidazole, N-dodecyl-2,6-dimethyl-morpholine, N-dodecyl-5-chloromethyl-2-oxazolidinone, N-dodecyl-2-pyrrolidinone, N-dodecyl hexamethyleneimine, N-dodecyl pyrrolidine, N-dodecyl-3-methyl-piperidine, N-dodecyl piperidine, N-dodecyl-4-methyl-piperidine and N-dodecyl-2-methyl-piperidine.

4. A microbicidal composition according to claim 1, wherein the N-alkyl heterocyclic compound is N-dodecyl morpholine.

5. A microbicidal composition according to claim 4 wherein (a) and (b) are present in a combined amount synergistically effective to control the growth of at least one microorganism selected from algae, fungi, and bacteria.

6. A microbicidal composition according to claim 1, wherein the N-alkyl heterocyclic compound is N-dodecyl imidazole.

7. A microbicidal composition according to claim 6 wherein (a) and (b) are present in a combined amount synergistically effective to control the growth of at least one microorganism selected from algae, fungi, and bacteria.

8. A microbicidal composition according to claim 1, wherein the composition is an aqueous formulation.

9. A method for controlling the growth of microorganisms on a substrate comprising the step of contacting a substrate susceptible to the growth of microorganisms with (a) 2-(Thiocyanomethylthio)benzothiazole (TCMTB) and (b) an N-alkyl heterocyclic compound of the formula:

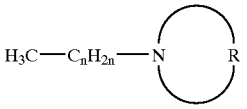

wherein n [may be from 5 to 17] *varies from 9 to 15*, the heterocyclic ring defined by

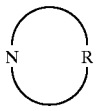

is a substituted or unsubstituted ring having four to eight members, and the TCMTB (a) and the N-alkyl heterocyclic compound (b) are present in a combined amount effective to control the growth of at least one microorganism on the substrate and the amount of the N-alkyl heterocyclic compound (b) present potentiates the microbicidal activity of the TCMTB (a).

10. A method according to claim 9, wherein [n varies from 9 to 15, and] the heterocyclic ring is selected from the group consisting of pyrrolidinyl, 2-pyrrolidinonyl, pyrrolinyl, pyrazolidinyl, pyrazolinyl, pyrazolyl, imidazolidinyl, imidazolinyl, imidazolyl, oxazolidinonyl, piperadinyl, piperazinyl, morpholinyl, hexamethyleneiminyl, and heptamethyleneiminyl.

11. A method according to claim 9, wherein the N-alkyl heterocyclic compound is selected from the group consisting of N-dodecyl morpholine, N-dodecyl imidazole, N-dodecyl-2,6-dimethyl-morpholine, N-dodecyl-5-chloromethyl-2-oxazolidinone, N-dodecyl-2-pyrrolidinone, N-dodecyl hexamethyleneimine, N-dodecyl pyrrolidine, N-dodecyl-3-methyl-piperidine, N-dodecyl piperiodine, N-dodecyl-4-methyl-piperidine and N-dodecyl-2-methyl-piperidine.

12. A method according to claim 9, wherein the N-alkyl heterocyclic compound is N-dodecyl morpholine.

13. A [method according to claim 12 wherein (a) and (b)] *microbicidal composition, comprising 2-(Thiocyanomethylthio) benzothiazole (TCMTB) and N-dodecyl morpholine, wherein the TCMTB and N-dodecyl morpholine* are present in a combined amount synergistically effective to control the growth of at least one microorganism selected from algae, fungi, and bacteria.

14. A [method according to claim 13, wherein (a) and (b)] *microbicidal composition, comprising 2-(Thiocyanomethylthio) benzothiazole (TCMTB) and N-dodecyl imidazole, wherein the TCMTB and N-dodecyl imidazole* are present in a combined amount synergistically effective to control the growth of at least one microorganism selected from algae, fungi, and bacteria.

15. A method according to claim 9, wherein the N-alkyl heterocyclic compound is N-dodecyl imidazole.

16. A method for controlling the growth of microorganisms on a hide during a leather tanning process comprising the step of contacting the leather with (a) 2-Thiocyanomethylthio)benzothiazole (TCMTB) and (b) an N-alkyl heterocyclic compound of the formula:

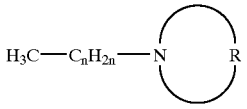

wherein n [may be from 5 to 17] *varies from 9 to 15*, the heterocyclic ring defined by

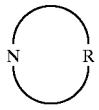

is a substituted or unsubstituted ring having four to eight members, and wherein the TCMTB (a) and the N-alkyl heterocyclic compound (b) are present in a combined amount effective to control the growth of at least one microorganism on the hide and the amount of the N-alkyl heterocyclic compound (b) present potentiates the microbicidal activity of the TCMTB (a).

17. A method according to claim 16, wherein the N-alkyl heterocyclic compound is N-dodecyl morpholine or N-dodecyl imidazole and the microorganism is algae, fungi, or bacteria.

18. A liquor for use in a leather-tanning process comprising (a) 2-(Thiocyanomethylthio)benzothiazole (TCMTB) and (b) an N-alkyl heterocyclic compound of the formula:

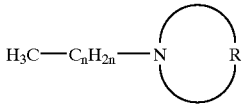

wherein n [may be from 5 to 17] *varies from 9 to 15*, the heterocyclic ring defined by

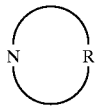

is a substituted or unsubstituted ring having four to eight members, the TCMTB (a) and the N-alkyl heterocyclic compound (b) are present in the liquor in a combined amount effective to control the growth of at least one microorganism on the leather, and the amount of the N-alkyl heterocyclic compound (b) present potentiates the microbicidal activity of the TCMTB (a); and the liquor is selected from a pickling liquor, a chrome-tanning liquor, a vegetable-tanning liquor, a post-tan washing liquor, a retanning liquor, a dye liquor, and a fat liquor.

19. A liquor according to claim 18, wherein the N-alkyl heterocyclic compound is N-dodecyl morpholine or N-dodecyl imidazole and the microorganism is algae, fungi, or bacteria.

20. A method for controlling the growth of microorganisms on a textile substrate in a textile manufacturing process comprising the step of contacting the textile substrate with (a) 2-(Thiocyanomethylthio)benzothiazole (TCMTB) and (b) an N-alkyl heterocyclic compound of the formula:

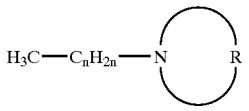

wherein n varies from [5 to 17] *9 to 15*, the heterocyclic ring defined by

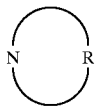

is a substituted or unsubstituted ring having four to eight members, and wherein the TCMTB (a) and the N-alkyl heterocyclic compound (b) are present in a combined amount effective to control the growth of at least one microorganism on the textile substrate and the amount of the N-alkyl heterocyclic compound (b) present potentiates the microbicidal activity of the TCMTB (a).

21. A method according to claim 20, wherein the N-alkyl heterocyclic compound is N-dodecyl morpholine, or N-dodecyl imidazole and the microorganism is algae, fungi, or bacteria.

22. A method for controlling the growth of microorganisms on lumber comprising the step of contacting the lumber with (a) 2-(Thiocyanomethylthio)benzothiazole (TCMTB) and (b) an N-alkyl heterocyclic compound of the formula:

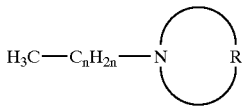

wherein n varies from [5 to 17] *9 to 15*, the heterocyclic ring defined by

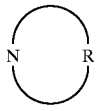

is a substituted or unsubstituted ring having four to eight members, and wherein the TCMTB (a) and the N-alkyl heterocyclic compound (b) are present in a combined amount effective to control the growth of at least one microorganism on the lumber and the amount of the N-alkyl heterocyclic compound (b) present potentiates the microbicidal activity of the TCMTB (a).

23. A method according to claim 22, wherein the N-alkyl heterocyclic compound is N-dodecyl morpholine or N-dodecyl imidazole and the microorganism is algae, fungi, or bacteria.

24. A method according to claim 22, wherein the contacting step comprises dipping the lumber in a bath containing the TCMTB and the N-alkyl heterocyclic compound.

25. A method according to claim 22, wherein the contacting step comprises spraying an aqueous formulation of the TCMTB and the N-alkyl heterocyclic compounds onto the lumber.

26. A method for controlling the growth of microorganisms on a seed or plant comprising the step of contacting the seed or plant with (a) 2-(Thiocyanomethylthio)benzothiazole (TCMTB) and (b) an N-alkyl heterocyclic compound of the formula:

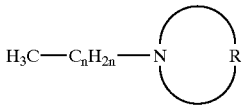

wherein n varies from [5 to 17] *9 to 15*, the heterocyclic ring defined by

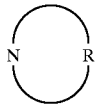

is a substituted or unsubstituted ring having four to eight members, and wherein the TCMTB (a) and the N-alkyl heterocyclic compound (b) are present in a combined amount effective to control the growth of at least one microorganism and the amount of the N-alkyl heterocyclic compound (b) present potentiates the microbicidal activity of the TCMTB (a).

27. A method according to claim 26, wherein the N-alkyl heterocyclic compound is N-dodecyl morpholine or N-dodecyl imidazole and the microorganism is algae, fungi, or bacteria.

28. A method according to claim 26, wherein the contacting step comprises drenching the soil surrounding a seed or plant with an aqueous formulation of the TCMTB and the N-alkyl heterocyclic compound.

29. A method according to claim 26, wherein the contacting step comprises spraying an aqueous formulation of the TCMTB and the N-alkyl heterocyclic compounds onto the seed or plant.

30. A method for controlling the growth of microorganisms in an aqueous system capable of supporting growth of a microorganism comprising the step of treating the aqueous system with (a) 2-(Thiocyanomethylthio)benzothiazole (TCMTB) mad (b) an N-alkyl heterocyclic compound of the formula:

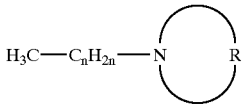

wherein n varies from [5 to 17] *9 to 15*, the heterocyclic ring defined by

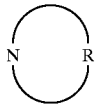

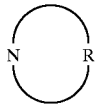

is a substituted or unsubstituted ring having four to eight members, and wherein the TCMTB (a) and the N-alkyl heterocyclic compound (b) are present in a combined amount effective to control the growth of at least one microorganism and the amount of the N-alkyl heterocyclic compound (b) present potentiates the microbicidal activity of the TCMTB (a).

31. A method according to claim 30, wherein the N-alkyl heterocyclic compound is N-dodecyl morpholine or N-dodecyl imidazole and the microorganism is algae, fungi, or bacteria.

32. A method according to claim 30, wherein said aqueous system is selected from the group consisting of a latex, a metal working fluid, an aqueous emulsion, an aqueous detergent, cooling water, and an aqueous resin formulation.

33. A method for controlling the growth of microorganisms on pulp or paper in a papermaking process, comprising the step of contacting the pulp or paper with (a) 2-(Thiocyanomethylthio)benzothiazole (TCMTB) and (b) an N-alkyl heterocyclic compound of the formula:

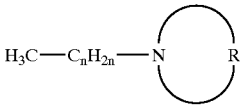

wherein n varies from [5 to 17] *9 to 15*, the heterocyclic ring defined by is a substituted or unsubstituted ring having four to eight members, and wherein the TCMTB (a) and the N-alkyl heterocyclic compound (b) are present in a combined amount effective to control the growth of at least one microorganism and the amount of the N-alkyl heterocyclic compound (b) present potentiates the microbicidal activity of the TCMTB (a).

34. A method according to claim 33, wherein wet-lap pulp is contacted by spraying an aqueous formulation of the TCMTB and the N-alkyl heterocyclic compound onto the pulp after the pulp leaves a press in the papermaking process.

35. A method according to claim 33, wherein wet-lap pulp is contacted by mixing the TCMTB and an N-alkyl heterocyclic compound into a pulp/white water mixture prior to reaching a formation wire in a papermaking process.

36. A method according to claim 33, wherein the TCMTB and the N-alkyl heterocyclic compound are incorporated into the body of the paper.

37. A method according to claim 33, wherein contacting step is accomplished by mixing the TCMTB and an N-alkyl heterocyclic compound into a coating composition and the coating composition is applied to the finished paper.

38. A method according to claim 33, wherein the N-alkyl heterocyclic compound is N-dodecyl morpholine or N-dodecyl imidazole and the microorganism is algae, fungi, or bacteria.

* * * * *